(12) United States Patent
Simpson et al.

(10) Patent No.: US 9,074,222 B2
(45) Date of Patent: Jul. 7, 2015

(54) DCX MINI-PROMOTERS

(71) Applicant: UNIVERSITY OF BRITISH COLUMBIA, Vancouver (CA)

(72) Inventors: Elizabeth M. Simpson, Vancouver (CA); Wyeth W. Wasserman, Vancouver (CA); Robert A. Holt, Vancouver (CA); Steven J. Jones, Vancouver (CA); Daniel Goldowitz, Vancouver (CA); Elodie Portales-Casamar, Vancouver (CA); Cletus D'Souza, Vancouver (CA); Vikramjit Chopra, Vancouver (CA); Charles de Leeuw, Vancouver (CA)

(73) Assignee: THE UNIVERSITY OF BRITISH COLUMBIA, Vancouver, B.C. (CA)

( * ) Notice: Subject to any disclaimer, the term of this patent is extended or adjusted under 35 U.S.C. 154(b) by 0 days.

(21) Appl. No.: 14/162,663

(22) Filed: Jan. 23, 2014

(65) Prior Publication Data

US 2014/0248701 A1    Sep. 4, 2014

Related U.S. Application Data

(60) Provisional application No. 61/756,876, filed on Jan. 25, 2013.

(51) Int. Cl.
*C12N 15/85*    (2006.01)
(52) U.S. Cl.
CPC ........................................ *C12N 15/85* (2013.01)
(58) Field of Classification Search
CPC .......................................................... C12N 15/85
See application file for complete search history.

(56) References Cited

U.S. PATENT DOCUMENTS 7,947,448 B2 * 5/2011 Couillard-Despres et al. . 800/14

OTHER PUBLICATIONS

Sequence Alignment—12209974-seq1 vs. 14162663-seq1 (2014).*
Sequence Alignment—12209974-seq1 vs. 14162663-seq2 (2014).*
Sequence Alignment—12209974-seq1 vs. 14162663-seq3 (2014).*
Sequence Alignment—14162663-seq1 vs. 14162663-seq4 (2014).*
Sequence Alignment—14162663-seq1 vs. 14162663-seq7 (2014).*
Couillard-Despres; et al. "Targeted transgene expression in neuronal precursors: watching young neurons in the old brain", Eur J Neurosci (Sep. 2006), 24(6):1535-1545.
Couillard-Despres; et al. "Doublecortin expression levels in adult brain reflect neurogenesis", Eur J Neurosci (Jan. 2005), 21(1):1-14.
Karl; et al. "Neuronal precursor-specific activity of a human doublecortin regulatory sequence", J Neurochem (Jan. 2005), 92(2):264-282.
Piens; et al. "A short upstream promoter region mediates transcriptional regulation of the mouse doublecortin gene in differentiating neurons", BMC Neurosci (May 2010), 11:64.
Wang; et al. "Rapid promoter analysis in developing mouse brain and genetic labeling of young neurons by doublecortin-DsRed-express", J Neuorsci Res (Dec. 2007), 85(16):3567-3573.

* cited by examiner

*Primary Examiner* — Scott Long
(74) *Attorney, Agent, or Firm* — Bozicevic, Field & Francis LLP; Pamela J. Sherwood

(57) ABSTRACT

Isolated polynucleotides comprising a DCX mini-promoters are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

18 Claims, 8 Drawing Sheets

(8 of 8 Drawing Sheet(s) Filed in Color)

Ple53-lacZ (*DCX*) Germline, N2 M, P55
tEMS7060, brain

Ple53-lacZ (*DCX*) Germline, N2 M, P55
tEMS7061, brain

Ple55-lacZ (*DCX*) Germline, N2 M, P87
tEMS7058, brain

Ple55-lacZ (*DCX*) Germline, N2 M, P61
tEMS7059, brain

Ple55-lacZ (DCX)
eye

_US 9,074,222 B2_

SEQUENCE LISTING

```
<160> NUMBER OF SEQ ID NOS: 8

<210> SEQ ID NO 1
<211> LENGTH: 3687
<212> TYPE: DNA
<213> ORGANISM: Homo sapiens
<220> FEATURE:
<221> NAME/KEY: misc_feature
<222> LOCATION: (1)..(637)
<223> OTHER INFORMATION: human DCX regulatory element #1
<220> FEATURE:
<221> NAME/KEY: misc_feature
<222> LOCATION: (638)..(1316)
<223> OTHER INFORMATION: human DCX regulatory element #2
<220> FEATURE:
<221> NAME/KEY: misc_feature
<222> LOCATION: (1317)..(3687)
<223> OTHER INFORMATION: human DCX basal promoter, corresponds to Ple302

<400> SEQUENCE: 1
tgtgactgaa aatgatattt gcccattcat tacttttag atacctcac attgatgctc      60 agcatctatt ttgataaaag gaagttgaag tgaccttcat atgctctgaa agaagtcaga    120
tacggggaaa gcactgaagc ctctggctcg ttgtctttgc ctcacactaa accatattta    180
ttctctttct cttttccata tgacatagct gtcttaattt ggttccactg atggtttgtg    240
tgagaaaggg actatttcag gatcctaaaa ttagcccaag aaagatgctg ccatctgttc    300
cccctccaaa tcaggttctt catgtcattg gttatactac taaagtgcca cctatattaa    360
tatctgggaa agaatgcagc caggcgtctc catcagacag atgcaccatt ctcttaagca    420
tagggagctg taaatataca acaaaaatgt tccaagggaa ttggaacagt ggctggttct    480
gttggctcta aagagaattc tggtctccca tcagaaaaga caagtgtgga ttagtatcag    540
tccatatatt ctacctctta aaatgccttt ggtgtttaaa caactatata gaaaaggtat    600
tcctaaaagg cggattcact atatatcaaa gttactgtcc cactcctcct tcaaccctct    660
cattttcaca cgtaggagtg gtaggtagag cagatgcagg tgacagaaag ctgaacccaa    720
gcagtccgat tgggaaattg attctcaaca ggaagggact tcgatctctg cttatctttt    780
ctcactcaaa tgcggcgtta gaccccaaga caaagctcag attgatgcag tccccacccc    840
acccttctcc tggcttcttt tctgtaagta atgctttcag tgtttggagt ctggcagctg    900
```

| | |
|---|---|
| caaggcctgg ttgctaggta acaatttctc agcacaaaga accttcagct gggaaggtca | 960 |
| ggtctatcag tgtgaaacag ctgtaaagaa ttttatttg tctcctcttg ttttggttaa | 1020 |
| tcacagggca gggaaccaaa atcaaacttt ccatagaaat gagagatacc ggagggtacc | 1080 |
| agtttagctg ctgctgattt tttgcagctc ttcaaatcac agcctttta cgctggctca | 1140 |
| atagagcccc aacaagcttg tcaggctgga agtggaggca ggaggaggag gggtcaggtg | 1200 |
| tttcctagcc tctttagtgc ctcaggcagg aaggacatag caaaaacatg agctgagaag | 1260 |
| ttaagtcctt ttcttcaaat ttaccagcag tttcttcaga ttagcgttgt cagatttgat | 1320 |
| agatttggga tgtccttttt acttctatct tccataatat tctaaaatta ttttcccttg | 1380 |
| ttttgttcct atcctacttc ctcttagtct actttgttga cttcattaaa aaacaaaaaa | 1440 |
| ccagttgttg gatacttgag ctaaactgcc ttaaagaatc tgcagatttt attttatttt | 1500 |
| ttttctctca agagggtaaa aggaagagag ctacaatttc taagaagcct ggcttggctg | 1560 |
| tctgagtctg gcccccaggc agattaggcc aaggttttgg ccaagtgaaa ttgccaattt | 1620 |
| tctaaaagaa agggctagca cattgctcat tagagcattc tgattttgtc tgcgcaatct | 1680 |
| ttctgctacc ccgcaatttc ctgttggtta taaatgaaac cttctagct gttaatgcag | 1740 |
| cctgtgaatt tttttaaaag catgtaatta atcataggag gttgggggga ttcactaagc | 1800 |
| ctgagttaca tgggagaagc tggacaaggc actaggacct agaaggcatc tatccaccct | 1860 |
| ggcaggaatt tcttgcttgg agctcagaca acaaaggcat agagagattg gttttctttc | 1920 |
| tctcagcatc tccacccaac cagcagaaaa ccggtgagtg gggcttttaa gtgattttca | 1980 |
| agaagaatgt aacagatgtc aaacgggaaa agcacgaggc aaagcctgct ctctctgtct | 2040 |
| ctctgtctcc tcttctcctt ttttgcctta ttctatccga ttttttccct aagcttctac | 2100 |
| ctgggatttt cctttggaaa agtgagtttg atgttccttt gttttcactg tgatgttaat | 2160 |
| ttagaataat actacctctg atcctaaagc aaagcaaagc cttactggca tgcctgggga | 2220 |
| aatgtttgct gcttgcctg aggaggtggg gtctcttacc actgcaggtt gtctgacaga | 2280 |
| gacaatgctg agctcagcat aggtcatggt gacattggaa aaaaggcgga attgagcctg | 2340 |
| gcagacccat taggcaccag tctttcttat ctcctgtcct cctggtccct tgcaaatata | 2400 |
| ttgatgtggc agtgtgtagc agctgagccc tgcttgcttt gtgagtcctt ttatccccat | 2460 |
| ctgtgagatg catgttaata gtttggctcg taggatgtca ctacatttgc tagcatttgt | 2520 |
| ggcttcagtt gtattgggtt tcatgttttg attgtttggg gttcttggtg ggggagggg | 2580 |
| ttaacagaa gggagaaaag caaagcctga caaatgacca tcttttctca gctaatgcac | 2640 |
| ctggcaata tacaagtttg gggtgaattg cctgctgtga gggtaaatgt cacttcaatt | 2700 |
| aaggtagaaa cccagaacaa tgaaggtgt gcttccttct aaaggtcccg tatgctgttc | 2760 |
| ggagagtcat ttgtgaatct ttcaacaatt aaattattcc attaagaggt gttgctgcat | 2820 |
| cagtggggag ggggtggagc acctgggggg gaaaaaaaag gattttgtga acaaatggaa | 2880 |
| ccggggaag acagagctag taacttgtta ataactttat ttttctaatc cttttttcccc | 2940 |
| ccagcttatt tcttatgaat gtcggatagc tgcaccagct tggtggggaa agggtttgat | 3000 |
| gaatagcaca aagacactgg ctgttccctg gaggctgtcc ctttaaagga gaatcttagt | 3060 |
| ttattctggg gggaggggat gcacacatta gagtaggaaa gagggcttgg aataaaatga | 3120 |
| aaacactccc ccttcatagt cattgtactg aaatgcaaag actgcttcct aagctggaga | 3180 |
| tgctaacctt gggtagctcc ttctgttctc ttcaagggga attttgtcag gctatggatt | 3240 |
| catttacaac tgttagtcat gtgggcatgt gtgaggaaac agatgccagt tttaatgtat | 3300 |

```
ttagcccgaa gttccaattt gataggagcc actgtcagta agtctcagga ttttcagcta    3360
tttcaaaatc tcccttctc ctctgtctgg aacagtgcca agagtgcctc cctctctatc     3420
tcttactccc aaccccaca accaccagca ccccgccca gcccctcctt cttctctatt      3480
aagatcaata ttcctgcagg tcaggggcaa gcagcagatg ggtcacaggc tttttcaac    3540 cagttctttt cacaagcagc agattgcaga tctggatctg gctaatattt aaaatcccctt  3600 cttttttcct tctccttgtc cctttttgtt tttgcctctc ttcacccca tcccttctc    3660 ccacgctcag gtctctgagg ttccacc                                        3687
```

<210> SEQ ID NO 2
<211> LENGTH: 3877
<212> TYPE: DNA
<213> ORGANISM: Homo sapiens
<220> FEATURE:
<221> NAME/KEY: misc_feature
<222> LOCATION: (1)..(1506)
<223> OTHER INFORMATION: human DCX regulatory element #3
<220> FEATURE:
<221> NAME/KEY: misc_feature
<222> LOCATION: (1507)..(3877)
<223> OTHER INFORMATION: human DCX basal promoter, corresponds to Ple302

<400> SEQUENCE: 2

```
gatgtaccca tgagaactcg ttctttcttc tctcctaacc ttcttcttgc atagcaaaat      60
atacacttac agagtagggg atattatgta aggaaatgca gtatgtttat ggtcattagt     120
attctgtcca gccatgttga ggtcagctcc taagtaacaa tttcagaata tctataatca     180
agctgtatgt cccttaccaa ctgggcagtc atgctttttt tttcctgtcc tcaaccaacc     240
actaaggaac atttagaggt catgcctctc atgcctacac tctcctgaaa agttagcatc     300
cttcctaaat tctagcaacc tgggaggcaa tgggtctgat gcacactcta gtctttggtt     360
tgccgtaaat cagtttgcac tccttttgctt cccttggact cagtttgcag agaatgagct    420
tatatccttt tgcttccttt ggactggagt ctcaggaagc ctgggaaggg gggtacagtt     480
aagcctctgg gattccacga cagctgccag cattctggcc cgggtgtcac tgctcattaa     540
ctgtgtccaa cctggaatgt tcatagact gtctgagcta aagagacct cagaaatcaa       600 ctagtctaga gactcttaat ttgggatcta tagacaagct tcaaggaat ccttaacccc      660 cctaaactat atagaaaact agctatctat gggcatatat gcattttttc tagggagaag    720
acctacagct ttcatcaaat tctctaaagg gcttgtgaca caaaaagat atagatctca     780 aaaggctcta gatcagcacc ttctccttat agcagaagaa acagaccag agagaaagca     840 gtgagccagt gtcaagttgt aacctagaat gcaggtagac aataactttc ttttcttttc    900
ttttcttttc ttttttttt tttaacaaac ctttccttcc cctacgtgat tcaaaagcaa    960
tatccctctc atgctttgtg tctagcagac accaggaaac tgttaaatgc aacagataac   1020
tgtaatgggc cctacaagca cactctctta ttttaattga ccttactaaa cagaacctag   1080
agttgtgtgg ggcccagagc caaccttagg gcttaatggt gccaagggat caagcagggt   1140
ttttccaccc cagttctttc tgatgaatgg agttctgtct cgtctctgtt tctctgagcc   1200
aatttgtccc cagggccttg tggaagggca ggtgtcagtc ctgggcatgt actcaacagc   1260
ccaactccag cgcctctgca gctgttctca tccttgagag gcccccagtg ggagctgaca   1320
cagactcttg gaaaaatggc aaagacaaaa taaggaaaga acacccttga gcatcgaggg   1380
gctgccagcc ttccaatcag gctggtattg cctagctcag gttattaaat caccactagc   1440
```

```
tccaggtaaa atagggtaga aagtcttatt ccttcacatc tcccctctgt gcccttcttt    1500
cccatatgat agatttggga tgtccttttt acttctatct tccataatat tctaaaatta    1560
ttttcccttg ttttgttcct atcctacttc ctcttagtct actttgttga cttcattaaa    1620
aaacaaaaaa ccagtgttg gatacttgag ctaaactgcc ttaaagaatc tgcagatttt    1680 atttatttt ttttctctca agagggtaaa aggaagagag ctacaatttc taagaagcct    1740
ggcttggctg tctgagtctg gcccccaggc agattaggcc aaggttttgg ccaagtgaaa    1800
ttgccaattt tctaaaagaa agggctagca cattgctcat tagagcattc tgattttgtc    1860
tgcgcaatct ttctgctacc ccgcaatttc ctgttggtta taaatgaaac ctttctagct    1920
gttaatgcag cctgtgaatt tttttaaaag catgtaatta atcataggag gttgggggga    1980
ttcactaagc ctgagttaca tgggagaagc tggacaaggc actaggacct agaaggcatc    2040
tatccaccct ggcaggaatt tcttgcttgg agctcagaca acaaaggcat agagagattg    2100
gttttctttc tctcagcatc tccacccaac cagcagaaaa ccggtgagtg gggcttttaa    2160 gtgatttca agaagaatgt aacagatgtc aaacgggaaa agcacaaggc aaagcctgct    2220
ctctctgtct ctctgtctcc tcttctcctt ttttgcctta ttctatccga ttttttccct    2280
aagcttctac ctgggatttt cctttggaaa agtgagtttg atgttccttt gttttcactg    2340
tgatgttaat ttagaataat actacctctg atcctaaagc aaagcaaagc cttactggca    2400
tgcctgggga atgtttgct gcttgccttg aggaggtggg gtctcttacc actgcaggtt    2460
gtctgacaga acaatgctg agctcagcat aggtcatggt gacattggaa aaaaggcgga    2520
attgagcctg gcagacccat taggcaccag tctttcttat ctcctgtcct cctggtccct    2580
tgcaaatata ttgatgtggc agtgtgtagc agctgagccc tgcttgcttt gtgagtcctt    2640
ttatccccat ctgtgagatg catgttaata gtttggctcg taggatgtca ctacatttgc    2700
tagcatttgt ggcttcagtt gtattgggtt tcatgttttg attgtttggg gttcttggtg    2760
ggggaggggg ttcaacagaa gggagaaaag caaagcctga caaatgacca tcttttctca    2820
gctaatgcac ctgggcaata tacaagtttg gggtgaattg cctgctgtga gggtaaatgt    2880
cacttcaatt aaggtagaaa cccagaacaa tgaaaggtgt gcttccttct aaaggtcccg    2940
tatgctgttc ggagagtcat ttgtgaatct ttcaacaatt aaattattcc attaagaggt    3000
gttgctgcat cagtggggag ggggtggagc acctgggggg gaaaaaaaag gattttgtga    3060
acaaatggaa ccgggggaag acagagctag taacttgtta ataacttat ttttctaatc    3120 cttttttcccc ccagcttatt tcttatgaat gtcggatagc tgcaccagct tggtggggaa    3180
agggtttgat gaatagcaca aagacactgg ctgttccctg gaggccgtcc ctttaaagga    3240
gaatcttagt ttattctggg gggaggggat gcacacatta gagtaggaaa gagggcttgg    3300
aataaaatga aaacactccc ccttcatagt cattgtactg aaatgcaaag actgcttcct    3360
aagctggaga tgctaacctt gggtagctcc ttctgttctc ttcaagggga attttgtcag    3420
gctatggatt catttacaac tgttagtcat gtgggcatgt gtgaggaaac agatgccagt    3480
tttaatgtat ttagcccgaa gttccaattt gataggagcc actgtcagta agtctcagga    3540
ttttcagcta tttcaaaatc tccccttctc ctctgtctgg aacagtgcca agagtgcctc    3600
cctctctatc tcttactccc aaccccacca accaccagca ccccgcccca gcccctcctt    3660
cttctctatt aagatcaata ttcctgcagg tcagggcaa gcagcagatg ggtcacaggc    3720
ttttttcaac cagttctttt cacaagcagc agattgcaga tctggatctg gctaatattt    3780 aaaatcccttt cttttttcct tctccttgtc ccttttttgtt tttgcctctc ttcacccccca    3840
``` tcccttctc ccacgctcag gtctctgagg ttccacc    3877

<210> SEQ ID NO 3
<211> LENGTH: 3520
<212> TYPE: DNA
<213> ORGANISM: Homo sapiens

<400> SEQUENCE: 3

| | | | | | |
|---|---|---|---|---|---|
| ggaacaccta | ttaatgccca | catatctcaa | acaaggaaat | attgatcctg | cctatccctc | 60 |
| tgctctctat | tatatataaa | gcaaacaaag | tcatttatcc | taggctgtct | cataaaaaca | 120 |
| ttttgtagct | tccacagtag | cattgcaaag | cctatattat | gaggaatttt | cctctgaaat | 180 |
| acattccaaa | tggttcgtgt | ttaagtttta | ttatcccatc | cattgttgta | tcttcaccag | 240 |
| aaataaaatg | atttttagtt | ctgatgcaaa | attaattgct | acatatttac | tgaatgctta | 300 |
| tgatgtgcaa | gaaagaagtt | ttaagacatt | agctttgttg | gaatttccat | attttcctgc | 360 |
| ccttattcct | tgattttct | tgcctctag | cctgaataat | gttgattttt | catgaggttg | 420 |
| ccacaaggta | aggcaacaac | acatggaaga | aaatagggca | gacacatgca | ttcccctgag | 480 |
| gtacttgtat | agtaaccaag | aaatcagcag | caaggtgttg | ggggactta | actaggtagg | 540 |
| ttgcacattt | gaggctatcc | actcaactaa | cagacagttc | caggctttgc | tgagtcaaca | 600 |
| cctttcacag | aagaaagacc | atcatatatt | ttatcccact | tggcggcagc | ttacaataaa | 660 |
| acacatgcag | agaaaatgct | taaatataaa | agttcaacag | cactatataa | aaggaagggt | 720 |
| taattatact | aggaatcaga | tataaaataa | ttactgagca | tgctcttagc | tctgagcttc | 780 |
| ctggaagcca | agcaaaaata | gaaccatgat | agttcaaggc | tgctacatat | tgatgcatgt | 840 |
| agcttcaatt | gtgaagatgg | tagcatcccc | ctaccccatt | taacctctca | cctttctctt | 900 |
| ttgttttata | gttcggcctg | atctaattag | ttcaatttgg | atgcttcctt | gagttttttt | 960 |
| tgtaacatat | tttatataaa | gaagtcagtt | agtgacaaat | aagcagtttg | aggagaaatc | 1020 |
| tgttaatatt | tattttgtag | ccatcagatt | tacttcacat | agaaaggtct | ttgggttggg | 1080 |
| tttgaacttc | caaactctca | aaggtaaatg | ccacattaac | ctttcattaa | ccaaattctt | 1140 |
| acaccaagct | gatagattg | ggatgtcctt | tttacttcta | tcttccataa | tattctaaaa | 1200 |
| ttatttccc | ttgttttgtt | cctatcctac | ttcctcttag | tctactttgt | tgacttcatt | 1260 |
| aaaaaacaaa | aaaccagttg | ttggatactt | gagctaaact | gccttaaaga | atctgcagat | 1320 |
| tttatttat | ttttttctc | tcaagagggt | aaaaggaaga | gagctacaat | ttctaagaag | 1380 |
| cctggcttgg | ctgtctgagt | ctggccccca | ggcagattag | gccaaggttt | tggccaagtg | 1440 |
| aaattgccaa | ttttctaaaa | gaaagggcta | gcacattgct | cattagagca | ttctgatttt | 1500 |
| gtctgcgcaa | tctttctgct | accccgcaat | ttcctgttgg | ttataaatga | aaccttctca | 1560 |
| gctgttaatg | cagcctgtga | attttttaa | aagcatgtaa | ttaatcatag | gaggttgggg | 1620 |
| ggattcacta | agcctgagtt | acatgggaga | agctggacaa | ggcactagga | cctagaaggc | 1680 |
| atctatccac | cctggcagga | atttcttgct | tggagctcag | acaacaaagg | catagagaga | 1740 |
| ttggttttct | ttctctcagc | atctccaccc | aaccagcaga | aaaccggtga | gtggggcttt | 1800 |
| taagtgattt | tcaagaagaa | tgtaacagat | gtcaaacggg | aaaagcacaa | ggcaaagcct | 1860 |
| gctctctctg | tctctctgtc | tcctcttctc | ctttttgcc | ttattctatc | cgatttttc | 1920 |
| cctaagcttc | tacctgggat | tttccttgg | aaaagtgagt | ttgatgttcc | tttgttttca | 1980 |
| ctgtgatgtt | aatttagaat | aatactacct | ctgatcctaa | agcaaagcaa | agccttactg | 2040 |

```
gcatgcctgg ggaaatgttt gctgcttgcc ttgaggaggt ggggtctctt accactgcag    2100
gttgtctgac agagacaatg ctgagctcag cataggtcat ggtgacattg gaaaaaaggc    2160
ggaattgagc ctggcagacc cattaggcac cagtcttct tatctcctgt cctcctggtc    2220
ccttgcaaat atattgatgt ggcagtgtgt agcagctgag ccctgcttgc tttgtgagtc    2280 ctttatccc catctgtgag atgcatgtta atagtttggc tcgtaggatg tcactacatt    2340
tgctagcatt tgtggcttca gttgtattgg gtttcatgtt ttgattgttt ggggttcttg    2400 gtggggagg gggttcaaca gaagggagaa aagcaaagcc tgacaaatga ccatcttttc    2460
tcagctaatg cacctgggca atatacaagt ttggggtgaa ttgcctgctg tgagggtaaa    2520
tgtcacttca attaaggtag aaacccagaa caatgaaagg tgtgcttcct tctaaaggtc    2580
ccgtatgctg ttcggagagt catttgtgaa tctttcaaca attaaattat tccattaaga    2640
ggtgttgctg catcagtggg gagggggtgg agcacctggg ggggaaaaaa aaggatttg    2700 tgaacaaatg gaaccggggg aagacagagc tagtaacttg ttaaataact tattttttcta    2760 atccttttc ccccagctt atttcttatg aatgtcggat agctgcacca gcttggtggg    2820
gaaagggttt gatgaatagc acaaagacac tggctgttcc ctggaggctg tcccttaaa    2880 ggagaatctt agtttattct gggggaggg gatgcacaca ttagagtagg aaagagggct    2940
tggaataaaa tgaaaacact cccccttcat agtcattgta ctgaaatgca aagactgctt    3000
cctaagctgg agatgctaac cttgggtagc tccttctgtt ctcttcaagg ggaattttgt    3060
caggctatgg attcatttac aactgttagt catgtgggca tgtgtgagga acagatgcc    3120 agttttaatg tatttagccc gaagttccaa tttgatagga gccactgtca gtaagtctca    3180
ggattttcag ctatttcaaa atctccccctt ctcctctgtc tggaacagtg ccaagagtgc    3240
ctccctctct atctcttact cccaaccccc acaaccacca gcaccccgc ccagccctc    3300 cttcttctct attaagatca atattcctgc aggtcagggg caagcagcag atgggtcaca    3360
ggcttttttc aaccagttct tttcacaagc agcagattgc agatctggat ctggctaata    3420
tttaaaatcc cttctttttt ccttctcctt gtccttttt gttttgcct ctcttcaccc    3480 ccatcccttt ctcccacgct caggtctctg aggttccacc                         3520

<210> SEQ ID NO 4
<211> LENGTH: 2359
<212> TYPE: DNA
<213> ORGANISM: Homo sapiens

<400> SEQUENCE: 4
gatgtccttt ttacttctat cttccataat attctaaaat tattttccct tgttttgttc      60
ctatcctact tcctcttagt ctactttgtt gacttcatta aaaaacaaaa aaccagttgt     120
tggatacttg agctaaactg ccttaaagaa tctgcagatt ttatttttatt ttttttctct     180 caagagggta aaaggaagag agctacaatt tctaagaagc ctggcttggc tgtctgagtc     240
tggcccccag gcagattagg ccaaggtttt ggccaagtga aattgccaat tttctaaaag     300
aaagggctag cacattgctc attagagcat tctgattttg tctgcgcaat ctttctgcta     360
ccccgcaatt tcctgttggt tataaatgaa acctttctag ctgttaatgc agcctgtgaa     420
tttttttaaa agcatgtaat taatcatagg aggttggggg gattcactaa gcctgagtta     480
catgggagaa gctggacaag gcactaggac ctagaaggca tctatccacc ctggcaggaa     540
tttcttgctt ggagctcaga caacaaaggc atagagagat tggtttttctt tctctcagca     600 tctccaccca accagcagaa aaccggtgag tggggctttt aagtgatttt caagaagaat     660
```

-continued

| | |
|---|---|
| gtaacagatg tcaaacggga aaagcacaag gcaaagcctg ctctctctgt ctctctgtct | 720 |
| cctcttctcc ttttttgcct tattctatcc gattttttcc ctaagcttct acctgggatt | 780 |
| ttcctttgga aaagtgagtt tgatgttcct ttgttttcac tgtgatgtta atttagaata | 840 |
| atactacctc tgatcctaaa gcaaagcaaa gccttactgg catgcctggg aaatgtttg | 900 |
| ctgcttgcct tgaggaggtg gggtctctta ccactgcagg ttgtctgaca gagacaatgc | 960 |
| tgagctcagc ataggtcatg gtgacattgg aaaaaaggcg gaattgagcc tggcagaccc | 1020 |
| attaggcacc agtctttctt atctcctgtc ctcctggtcc cttgcaaata tattgatgtg | 1080 |
| gcagtgtgta gcagctgagc cctgcttgct ttgtgagtcc ttttatcccc atctgtgaga | 1140 |
| tgcatgttaa tagtttggct cgtaggatgt cactacatt gctagcattt gtggcttcag | 1200 |
| ttgtattggg tttcatgttt tgattgtttg gggttcttgg tgggggaggg ggttcaacag | 1260 |
| aagggagaaa agcaaagcct gacaaatgac catcttttct cagctaatgc acctgggcaa | 1320 |
| tatacaagtt tggggtgaat tgcctgctgt gagggtaaat gtcacttcaa ttaaggtaga | 1380 |
| aacccagaac aatgaaaggt gtgcttcctt ctaaaggtcc cgtatgctgt tcggagagtc | 1440 |
| atttgtgaat ctttcaacaa ttaaattatt ccattaagag gtgttgctgc atcagtgggg | 1500 |
| aggggtgga gcacctgggg gggaaaaaaa aggatttgt gaacaaatgg aaccggggga | 1560 |
| agacagagct agtaacttgt taaataactt attttctaa tcctttttcc ccccagctta | 1620 |
| tttcttatga atgtcggata gctgcaccag cttggtgggg aaagggtttg atgaatagca | 1680 |
| caaagacact ggctgttccc tggaggctgt cccttttaaag gagaatctta gtttattctg | 1740 |
| gggggagggg atgcacacat tagagtagga aagagggctt ggaataaaat gaaaacactc | 1800 |
| cccctttcata gtcattgtac tgaaatgcaa agactgcttc ctaagctgga gatgctaacc | 1860 |
| ttgggtagct ccttctgttc tcttcaaggg gaattttgtc aggctatgga ttcatttaca | 1920 |
| actgttagtc atgtgggcat gtgtgaggaa acagatgcca gttttaatgt atttagcccg | 1980 |
| aagttccaat tgataggag ccactgtcag taagtctcag gattttcagc tatttcaaaa | 2040 |
| tctcccttc tcctctgtct ggaacagtgc caagagtgcc tccctctcta tctcttactc | 2100 |
| ccaacccca caaccaccag cacccccgcc cagcccctcc ttcttctcta ttaagatcaa | 2160 |
| tattcctgca ggtcagggc aagcagcaga tgggtcacag gctttttttca accagttctt | 2220 |
| ttcacaagca gcagattgca gatctggatc tggctaatat ttaaaatccc ttctttttc | 2280 |
| cttctccttg tcccttttg ttttgcctc tcttcacccc catccctttc tcccacgctc | 2340 |
| aggtctctga ggttccacc | 2359 |

<210> SEQ ID NO 5
<211> LENGTH: 1000
<212> TYPE: DNA
<213> ORGANISM: Homo sapiens

<400> SEQUENCE: 5

| | |
|---|---|
| aagccaagca aaaatagaac catgatagtt caaggctgct acatattgat gcatgtagct | 60 |
| tcaattgtga agatggtagc atcccctac cccatttaac ctctcacctt tctcttttgt | 120 |
| tttatagttc ggcctgatct aattagttca atttggatgc ttccttgagt ttttttttgta | 180 |
| acatatttta tataaagaag tcagttagtg acaaataagc agtttgagga gaaatctgtt | 240 |
| aatatttatt ttgtagccat cagatttact tcacatagaa aggtctttgg gttgggtttg | 300 |
| aacttccaaa ctctcaaagg taaatgccac attaacctt cattaaccaa attcttacac | 360 |

| | |
|---|---|
| caagctgata gatttgggat gtccttttta cttctatctt ccataatatt ctaaaattat | 420 |
| tttcccttgt tttgttccta tcctacttcc tcttagtcta ctttgttgac ttcattaaaa | 480 |
| aacaaaaaac cagttgttgg atacttgagc taaactgcct taaagaatct gcagatttta | 540 |
| ttttatttt tttctctcaa gagggtaaaa ggaagagagc tacaatttct aagaagcctg | 600 |
| gcttggctgt ctgagtctgg cccccaggca gattaggcca aggttttggc caagtgaaat | 660 |
| tgccaatttt ctaaaagaaa gggctagcac attgctcatt agagcattct gattttgtct | 720 |
| gcgcaatctt tctgctaccc cgcaatttcc tgttggttat aaatgaaacc tttctagctg | 780 |
| ttaatgcagc ctgtgaattt ttttaaaagc atgtaattaa tcataggagg ttgggggat | 840 |
| tcactaagcc tgagttacat gggagaagct ggacaaggca ctaggaccta gaaggcatct | 900 |
| atccaccctg gcaggaattt cttgcttgga gctcagacaa caaaggcata gagagattgg | 960 |
| ttttctttct ctcagcatct ccacccaacc agcagaaaac | 1000 |

<210> SEQ ID NO 6
<211> LENGTH: 637
<212> TYPE: DNA
<213> ORGANISM: Homo sapiens

<400> SEQUENCE: 6

| | |
|---|---|
| tgtgactgaa aatgatattt gcccattcat tactttttag ataccctcac attgatgctc | 60 |
| agcatctatt ttgataaaag gaagttgaag tgaccttcat atgctctgaa agaagtcaga | 120 |
| tacggggaaa gcactgaagc ctctggctcg ttgtctttgc ctcacactaa accatattta | 180 |
| ttctctttct cttttccata tgacatagct gtcttaattt ggttccactg atggtttgtg | 240 |
| tgagaaaggg actatttcag gatcctaaaa ttagcccaag aaagatgctg ccatctgttc | 300 |
| cccctccaaa tcaggttctt catgtcattg gttatactac taaagtgcca cctatattaa | 360 |
| tatctgggaa agaatgcagc caggcgtctc catcagacag atgcaccatt ctcttaagca | 420 |
| tagggagctg taaatataca acaaaaatgt tccaagggaa ttgaacagt ggctggttct | 480 |
| gttggctcta aagagaattc tggtctccca tcagaaaaga caagtgtgga ttagtatcag | 540 |
| tccatatatt ctacctctta aaatgccttt ggtgtttaaa caactatata gaaaaggtat | 600 |
| tcctaaaagg cggattcact atatatcaaa gttactg | 637 |

<210> SEQ ID NO 7
<211> LENGTH: 679
<212> TYPE: DNA
<213> ORGANISM: Homo sapiens

<400> SEQUENCE: 7

| | |
|---|---|
| tcccactcct ccttcaaccc tctcattttc acacgtagga gtggtaggta gagcagatgc | 60 |
| aggtgacaga aagctgaacc caagcagtcc gattgggaaa ttgattctca acaggaaggg | 120 |
| acttcgatct ctgcttatct tttctcactc aaatgcggcg ttagacccca agacaaagct | 180 |
| cagattgatg cagtccccac cccacccttc tcctggcttc ttttctgtaa gtaatgcttt | 240 |
| cagtgttggg agtctggcag ctgcaaggcc tggttgctag gtaacaattt ctcagcacaa | 300 |
| agaaccttca gctgggaagg tcaggtctat cagtgtgaaa cagctgtaaa gaattttat | 360 |
| ttgtctcctc ttgttttggt taatcacagg gcagggaacc aaaatcaaac tttccataga | 420 |
| aatgagagat accggagggt accagtttag ctgctgctga ttttttgcag ctcttcaaat | 480 |
| cacagccttt ttacgctggc tcaatagagc cccaacaagc ttgtcaggct ggaagtggag | 540 |
| gcaggaggag gagggtcag gtgtttccta gcctctttag tgcctcaggc aggaaggaca | 600 |

```
tagcaaaaac atgagctgag aagttaagtc cttttcttca aatttaccag cagtttcttc    660
agattagcgt tgtcagatt                                                 679

<210> SEQ ID NO 8
<211> LENGTH: 1506
<212> TYPE: DNA
<213> ORGANISM: Homo sapiens

<400> SEQUENCE: 8
gatgtaccca tgagaactcg ttctttcttc tctcctaacc ttcttcttgc atagcaaaat     60
atacacttac agagtagggg atattatgta aggaaatgca gtatgtttat ggtcattagt    120
attctgtcca gccatgttga ggtcagctcc taagtaacaa tttcagaata tctataatca    180
agctgtatgt cccttaccaa ctgggcagtc atgctttttt tttcctgtcc tcaaccaacc    240
actaaggaac atttagaggt catgcctctc atgcctacac tctcctgaaa agttagcatc    300
cttcctaaat tctagcaacc tgggaggcaa tgggtctgat gcacactcta gtctttggtt    360
tgccgtaaat cagtttgcac tcctttgctt cccttggact cagtttgcag agaatgagct    420
tatatccttt tgcttccttt ggactggagt ctcaggaagc ctgggaaggg gggtacagtt    480
aagcctctgg gattccacga cagctgccag cattctggcc cgggtgtcac tgctcattaa    540
ctgtgtccaa cctggaatgt ttcatagact gtctgagcta aagagacct cagaaatcaa     600 ctagtctaga gactcttaat ttgggatcta tagacaagct tcaaggaat ccttaacccc     660 cctaaactat atagaaaact agctatctat gggcatatat gcattttttc tagggagaag    720
acctacagct ttcatcaaat tctctaaagg gcttgtgaca caaaaaagat atagatctca    780
aaaggctcta gatcagcacc ttctccttat agcagaagaa acagacccag agagaaagca    840
gtgagccagt gtcaagttgt aacctagaat gcaggtagac aataactttc ttttcttttc    900
ttttcttttc tttttttttt tttaacaaac ctttccttcc cctacgtgat tcaaaagcaa    960
tatccctctc atgctttgtg tctagcagac accaggaaac tgttaaatgc aacagataac   1020
tgtaatgggc cctacaagca cactctctta ttttaattga ccttactaaa cagaacctag   1080
agttgtgtgg ggcccagagc caaccttagg gcttaatggt gccaagggat caagcagggt   1140
ttttccaccc cagttctttc tgatgaatgg agttctgtct cgtctctgtt tctctgagcc   1200
aatttgtccc cagggccttg tggaagggca ggtgtcagtc ctgggcatgt actcaacagc   1260
ccaactccag cgcctctgca gctgttctca tccttgagag gccccagtg ggagctgaca    1320 cagactcttg gaaaaatggc aaagacaaaa taaggaaaga acacccttga gcatcgaggg   1380
gctgccagcc ttccaatcag gctggtattg cctagctcag gttattaaat caccactagc   1440
tccaggtaaa atagggtaga aagtcttatt ccttcacatc tcccctctgt gcccttcttt   1500
cccata                                                             1506
```

DCX MINI-PROMOTERS

FIELD OF THE INVENTION

The invention relates to gene promoters and regulatory elements. More specifically, the invention relates to novel DCX promoter compositions and related methods.

BACKGROUND

There is a need for characterized human DCX promoters for gene expression, for instance in human gene therapy applications. It is in particular useful to identify small promoter elements that are sufficient to drive expression in certain cell types, for instance retinal ganglion cells. Such small promoter elements, or "mini-promoters" are particularly useful in certain applications, for instance they are more amenable to insertion into viral vectors used in gene therapy applications.

DCX promoter elements (alternatively referred to as doublecortin) from different species are described in the art, including:

Couillard-Despres S, Winner B, Karl C, Lindemann G, Schmid P, Aigner R, Laemke J, Bogdahn U, Winkler J, Bischofberger J, et al. 2006. Targeted transgene expression in neuronal precursors: watching young neurons in the old brain. Eur J Neurosci 24: 1535-1545.

Couillard-Despres S, Winner B, Schaubeck S, Aigner R, Vroemen M, Weidner N, Bogdahn U, Winkler J, Kuhn H-G, Aigner L. 2005. Doublecortin expression levels in adult brain reflect neurogenesis. Eur J Neurosci 21: 1-14.

Karl C, Couillard-Depres S, Prang P, Munding M, Kilb W, Brigadski T, Plotz S, Mages W, Luhmann H, Winkler J, Bogdahn U, Aigner L. 2005. Neuronal precursor-specific activity of a human doublecortin regulatory sequence. Journal of Neurochemistry 92: 264-282.

Piens M, Muller M, Bodson M, Baudoin G, Plumier J C. 2010. A short upstream promoter region mediates transcriptional regulation of the mouse doublecortin gene in differentiating neurons. BMC Neuroscience 11: 64.

Wang X, Runxiang Q, Tsark W, Lu Q. 2007. Rapid promoter analysis in developing mouse brain and genetic labeling of young neurons by doublecortin-DsRed-express. J Neuro Res 85: 3567-3573.

SUMMARY OF THE INVENTION

The present invention provides novel nucleic acid sequence compositions and methods relating to minimal human DCX promoters. The invention is based in part on the surprising discovery that certain minimal DCX promoter elements are capable of expressing in specific cell types, for instance in cells of the brain or eye.

In one embodiment of the invention, there is provided an isolated nucleic acid fragment comprising a DCX mini-promoter, wherein the DCX mini-promoter comprises a DCX regulatory element operably linked in a non-native conformation to a DCX basal promoter. The DCX mini-promoter may have a nucleic acid sequence which is substantially similar in sequence and function to SEQ ID NO: 1 or 2. The DCX basal promoter may have a nucleic acid sequence which is substantially similar in sequence and function to SEQ ID NO: 3, 4, or 5. The DCX regulatory element may have a nucleic acid sequence which is substantially similar in sequence and function to SEQ ID NO: 6, 7, or 8. In other embodiments, there is provided an isolated nucleic acid fragment comprising a DCX mini-promoter, wherein the DCX mini-promoter comprises a DCX basal promoter. The DCX basal promoter may have a nucleic acid sequence which is substantially similar in sequence and function to SEQ ID NO: 3, 4, or 5. The DCX mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a DCX mini-promoter, wherein the DCX mini-promoter comprises a DCX regulatory element operably linked in a non-native conformation to a DCX basal promoter. The DCX mini-promoter may have a nucleic acid sequence which is substantially similar in sequence and function to SEQ ID NO: 1 or 2. The DCX basal promoter may have a nucleic acid sequence which is substantially similar in sequence and function to SEQ ID NO: 3, 4, or 5. The DCX regulatory element may have a nucleic acid sequence which is substantially similar in sequence and function to SEQ ID NO: 6, 7, or 8. In other embodiments, there is provided an expression vector comprising a DCX mini-promoter, wherein the DCX mini-promoter comprises a DCX basal promoter. The DCX basal promoter may have a nucleic acid sequence which is substantially similar in sequence and function to SEQ ID NO: 3, 4, or 5. The DCX mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising a DCX mini-promoter element, wherein the DCX mini-promoter element comprises a DCX regulatory element operably linked in a non-native conformation to a DCX basal promoter element. In another embodiment, the DCX mini-promoter comprises a DCX basal promoter. Cells of interest include, without limitation, cells of the peripheral or central nervous system and progenitors thereof, e.g. embryonic stem cells, neural stem cells, neurons, glial cells, astrocytes, microglial cells, etc; and/or cells in the eye and progenitors thereof, e.g. retinal cells, amacrine cells, etc. The DCX mini-promoter may have a nucleic acid sequence which is substantially similar in sequence and function to SEQ ID NO: 1-5. The DCX regulatory element may have a nucleic acid sequence which is substantially similar in sequence and function to SEQ ID NO: 6, 7, or 8. The DCX basal promoter may have a nucleic acid sequence which is substantially similar in sequence and function to SEQ ID NO: 3, 4, or 5. The DCX mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a DCX mini-promoter element, wherein the DCX mini-promoter element comprises a DCX regulatory element operably linked in a non-native conformation to a DCX basal promoter element, and wherein the expressible sequence comprises a reporter gene. In other embodiments, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4, or 5. In some embodiments, the cell is a peripheral or central nervous system cell or progenitors thereof, including, without limitation, embryonic stem cells, neural stem cells, glial cells, astrocytes, neurons and the like, and/or cells in the eye and progenitors thereof, e.g. retinal cells, retinal ganglion cells, retinal amacrine cells, etc. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a DCX mini-promoter element operably linked to an expressible sequence, wherein the DCX mini-promoter element comprises a DCX regulatory element operably linked in a non-native conformation to a DCX basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4, or 5. In some embodiments, the cell is a peripheral or central nervous system cell or progenitors thereof, including, without limitation, embryonic stem cells, neural stem cells, glial cells, neurons and the like. In some embodiments, the cell is an eye cell or progenitor thereof, including without limitation a retinal cell, a retinal ganglion cell, retinal amacrine cell, and the like.

In certain embodiments of the invention, there is thus provided a method of treatment of a subject having a disease or condition of the eye, the method comprising administering to the subject a therapeutically effective dose of a composition comprising a DCX mini-promoter element, wherein the DCX mini-promoter element comprises a DCX regulatory element operably linked in a non-native conformation to a DCX basal promoter element. In another embodiment, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4 or 5. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
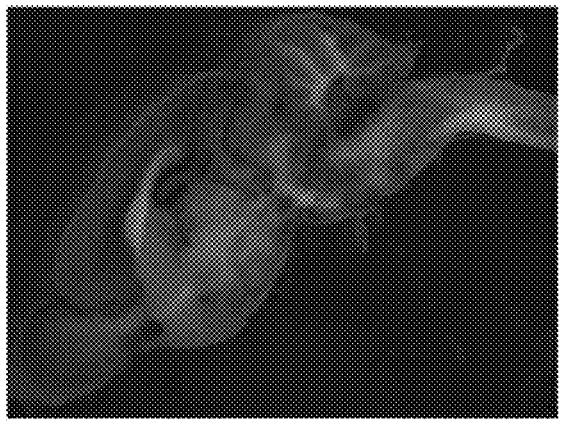
FIG. 1—Ple53-lacZ (DCX) expression in the brain. Mice were perfused, brains harvested and stained with X-gal. Expression of β-galactosidase from the MiniPromoter as detected by X-gal substrate is shown in blue. Neurogenic regions (SVZ, SGZ and RMS) are positive. Deeper layers of the cortex are stained, the olfactory bulbs, and in most mid- and hind-brain regions, including parts of the cerebellum. The medial and lateral habenula is strongly positive. Expression is absent in the striatum and low in the central to posterior thalamic regions. SVZ, subventricular zone; SGZ, subgranular zone; RMS, rostral migratory stream.
Figure 1:
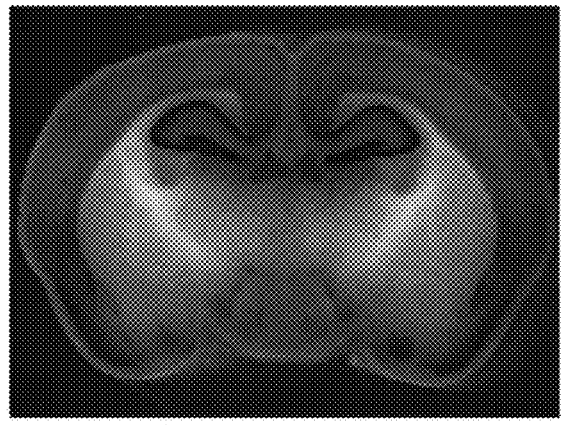
Figure 2:
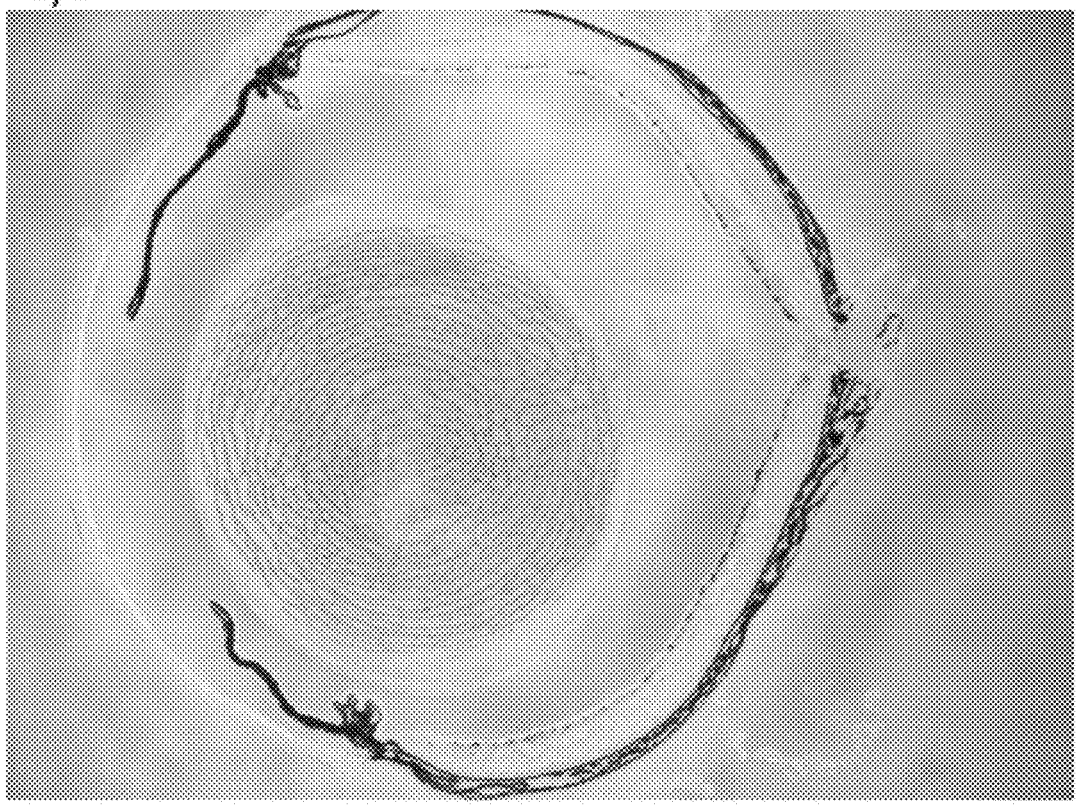
FIG. 2—Ple53-lacZ (DCX) expression in the eye. Eyes were perfused and stained with X-gal to detect β-galactosidase expression from the MiniPromoter. After staining, eyes were cryoprotected and sectioned at 12 μm and imaged. Expression is observed in the innermost aspect of the retina and optic nerve (not shown).
Figure 3:
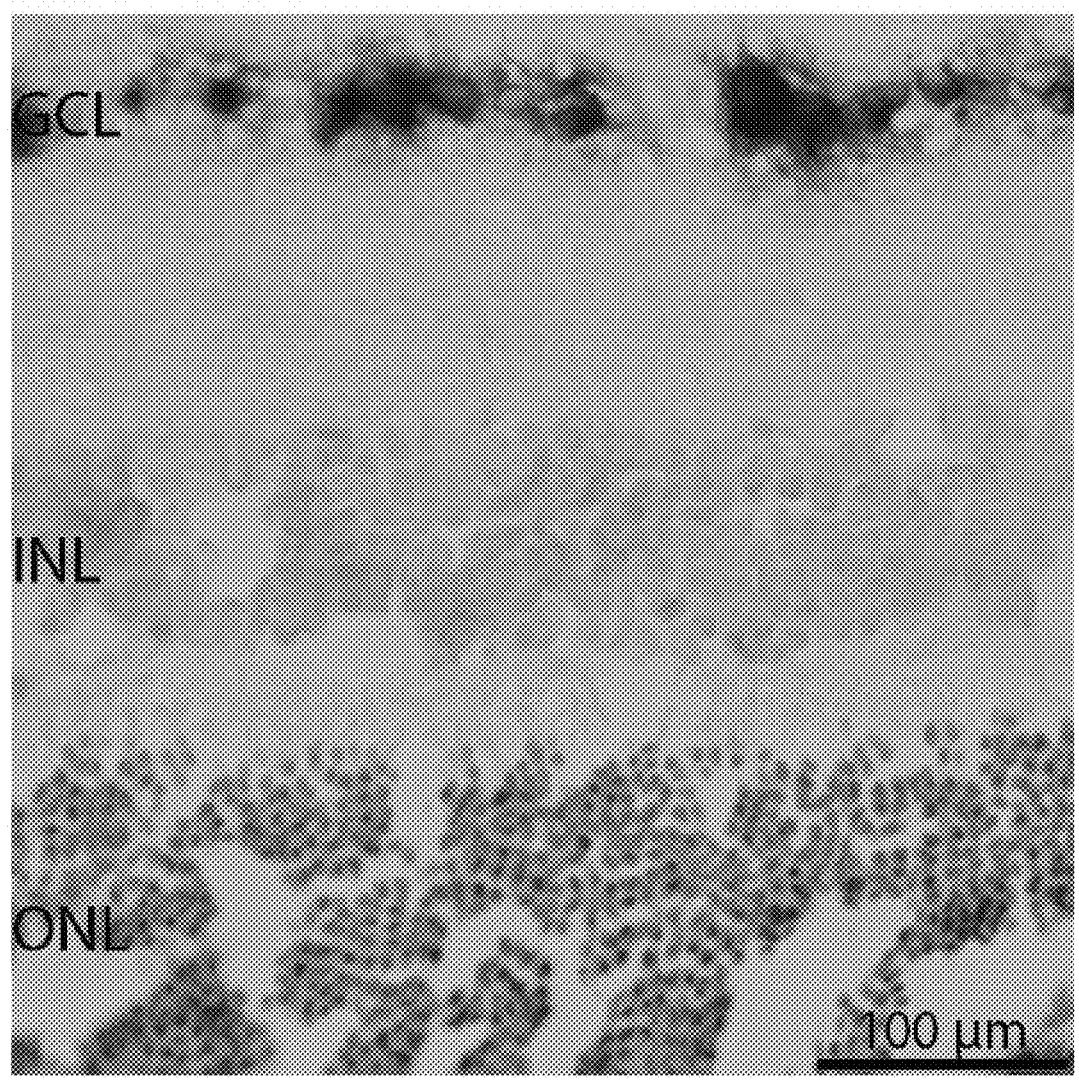
FIG. 3—Ple53-lacZ (DCX) expression is localized to the ganglion cell layer of the retina. Eyes were perfused and stained with X-gal to detect β-galactosidase expression from the MiniPromoter. After staining, eyes were cryoprotected and sectioned at 12 μm and counterstained with neutral red to indicate cell nuclei. The ganglion cell layer is where the predominant staining (blue) is observed. GCL, ganglion cell layer; INL, inner nuclear layer; ONL, outer nuclear layer. Scale bar 100 μm.

The compositions of the present invention include novel polynucleotides comprising DCX promoter elements (also referred to herein as DCX mini-promoters) as well as novel expression vectors comprising said DCX promoter elements (or mini-promoters). The present invention also includes various methods utilizing these novel DCX promoter (or mini-promoter) elements or expression vectors.

The term 'DCX' refers to the gene which encodes the DCX protein, also referred to as doublcortin, DC or DBCN. The human homolog of DCX is encoded by the human gene identified as EntrezGene #1641 and is located at chromosomal location Xq22.3-q23. The protein encoded by human DCX has the Protein Accession #O43602.3, however other protein accession numbers may also be assigned to this protein. DCX may also include other isoforms and/or splice variants. Other mammalian DCX homologs may include but are not limited to: *Rattus norvegicus* (EntrezGene #84394), *Mus musculus* (EntrezGene #13193).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'DCX basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 3, 4, or 5.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'DCX regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO: 6, 7, or 8. The present invention provides, in certain embodiments as described herein, different promoters of the DCX gene. In some embodiments, the DCX promoter comprises a DCX regulatory element operably linked to a DCX basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel DCX mini-promoters comprising a DCX regulatory element operably linked in a non-native conformation to a DCX basal promoter. In general the spacing between the DCX regulatory element and the DCX basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal DCX basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, John Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

DCX Mini-Promoters

The present invention herein provides novel DCX mini-promoter sequences which are capable of effecting transcriptional expression in a spatial and temporal fashion in the brain and/or eye. Certain DCX mini-promoters of the invention comprise minimal DCX promoter elements joined in a non-native configuration, thus providing advantageous characteristics. Other DCX mini-promoters of the invention comprise a minimal DCX basal promoter. Also provided are novel expression vector compositions comprising DCX mini-promoters which allow consistent specific spatiotemporal transcription of expression sequences. Also provided are novel methods utilizing these DCX mini-promoters and expression vectors.

The DCX promoters of the invention, as described herein, are referred to as 'mini-promoters' to reflect the fact that the mini-promoters comprise minimal DCX promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance a human DCX regulatory element corresponding to SEQ ID NO: 6, 7, or 8, and the human DCX basal promoter element corresponding to SEQ ID NO: 3, 4, or 5, or sequences with substantial functional and/or sequence equivalence, is altered. Additionally, the orientation of the different promoter elements may be altered—for instance the regulatory element corresponding to SEQ ID NO: 6, 7, or 8 may be inverted relative to the basal promoter element corresponding to SEQ ID NO: 3, 4, or 5. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that human DCX mini-promoters having a sequence corresponding to SEQ ID NO: 1 and 2 (also referred to in the Working Examples as Ple54 and Ple55), and which is comprised of one or more human DCX regulatory elements (for Ple54, the regulatory elements are SEQ ID NO: 6 and 7; for Ple55 the regulatory element is SEQ D NO: 8) operably linked in a non-native conformation to a human DCX basal promoter having a nucleic acid sequence corresponding to SEQ ID NO: 4, is capable of directing expression of an expressible sequence which is operably linked downstream of the DCX promoter in specific cell types in different regions of the brain and/or eye. The inventors have designed further constructs comprising DCX basal promoters, for instance those corresponding to SEQ ID NO: 3, 4 or 5. The DCX regulatory elements (SEQ ID NO'S: 6, 7, or 8) and DCX basal promoter element (SEQ ID NOS: 3, 4, or 5) have sequences which are identical to those found in the human DCX gene. It is within the skill of one in the art to locate and determine these relative positions based on published sequence information for this gene, for instance found in the Gen Bank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO: 1-5, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1-5 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In one embodiment of the invention, there is provided an isolated nucleic acid fragment comprising a DCX mini-promoter, wherein the DCX mini-promoter comprises a DCX regulatory element operably linked in a non-native conformation to a DCX basal promoter. The DCX mini-promoter may have a nucleic acid sequence which is substantially similar in sequence and function to SEQ ID NO: 1 or 2. The DCX basal promoter may have a nucleic acid sequence which is substantially similar in sequence and function to SEQ ID NO: 3, 4, or 5. The DCX regulatory element may have a nucleic acid sequence which is substantially similar in sequence and function to SEQ ID NO: 6, 7, or 8. In other embodiments, there is provided an isolated nucleic acid fragment comprising a DCX mini-promoter, wherein the DCX mini-promoter comprises a DCX basal promoter. The DCX basal promoter may have a nucleic acid sequence which is substantially similar in sequence and function to SEQ ID NO: 3, 4, or 5. The DCX mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising DCX mini-promoters which are capable of accomplishing this task. In one embodiment, there is provided an expression vector comprising a DCX mini-promoter, wherein the DCX mini-promoter comprises a DCX regulatory element operably linked in a non-native conformation to a DCX basal promoter. The DCX mini-promoter may have a nucleic acid sequence which is substantially similar in sequence and function to SEQ ID NO: 1 or 2. The DCX basal promoter may have a nucleic acid sequence which is substantially similar in sequence and function to SEQ ID NO: 3, 4, or 5. The DCX regulatory element may have a nucleic acid sequence which is substantially similar in sequence and function to SEQ ID NO: 6, 7, or 8. In other embodiments, there is provided an expression vector comprising a DCX mini-promoter, wherein the DCX mini-promoter comprises a DCX basal promoter. The DCX basal promoter may have a nucleic acid sequence which is substantially similar in sequence and function to SEQ ID NO: 3, 4, or 5. The DCX mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT, e.g. human HPRT, mouse HPRT, etc.

The inventors have herein demonstrated that expression vectors comprising novel DCX mini-promoter elements are capable of directing transcription of an expression sequence in specific cell types, for instance in gangion or amacrine cells in the retina (eye) or in neuronal cells in the brain. In one embodiment of the invention, there is thus provided a method for expressing a gene, protein, RNA interference molecule or the like in a cell, the method comprising introducing into the cell an expression vector comprising a DCX mini-promoter element, wherein the DCX mini-promoter element comprises a DCX regulatory element operably linked in a non-native conformation to a DCX basal promoter element. In another embodiment, the DCX mini-promoter comprises a DCX basal promoter. Cells of interest include, without limitation, cells of the peripheral or central nervous system and progenitors thereof, e.g. embryonic stem cells, neural stem cells, neurons, glial cells, astrocytes, microgial cells, etc; and/or cells in the eye and progenitors thereof, e.g. retinal cells, retinal ganglion cells, retinal amacrine cells etc. The DCX mini-promoter may have a nucleic acid sequence which is substantially similar in sequence and function to SEQ ID NO: 1-5. The DCX regulatory element may have a nucleic acid sequence which is substantially similar in sequence and function to SEQ ID NO: 6, 7, or 8. The DCX basal promoter may have a nucleic acid sequence which is substantially similar in sequence and function to SEQ ID NO: 3, 4 or 5. The DCX mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a DCX mini-promoter element, wherein the DCX mini-promoter element comprises a DCX regulatory element operably linked in a non-native conformation to a DCX basal promoter element, and wherein the expressible sequence comprises a reporter gene. In other embodiments, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4, or 5. The inventors have demonstrated that expression vectors comprising certain human DCX promoter elements are capable of expression in specific regions of the brain and eye, most notably retinal ganglion cells and amacrine cells in the eye. In some embodiments, the cell is a peripheral or central nervous system cell or progenitors thereof, including, without limitation, embryonic stem cells, neural stem cells, glial cell, neuronal cells, astrocytes, and the like. In some embodiments, the cell is a cell of the eye and progenitors thereof, including without limitation retinal cells, retinal ganglion cells, retinal amacrine cells, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell, the method comprising: 1) introducing into the cell a expression vector comprising a DCX mini-promoter element operably linked to an expressible sequence, wherein the DCX mini-promoter element comprises a DCX regulatory element operably linked in a non-native conformation to a DCX basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4, or 5. In such a fashion, one may be able to follow the development of a parent cell as it differentiates into more mature cells. As an example, one could introduce an expression vector comprising the aforementioned DCX mini-promoter elements into a pluripotent stem cell, monitor the expression of the reporter gene that is being expressed by the DCX promoter elements during the maturation and differentiation of the stem cell and thus determine the state of maturation, for instance in the differentiation of the pluripotent stem cell into a specific brain or retinal cell type. The inventors have demonstrated that the DCX mini-promoter elements described herein direct transcriptional expression in certain brain and retinal cell types, and so detection of reporter gene expression in a cell would thus be indicative of the cellular identity of the cell as being a certain type of brain or retinal cell.

The inventors have herein demonstrated that certain DCX mini-promoter elements of the present invention are capable of driving expression in retinal ganglion and retinal amacrine cells. This surprising expression pattern provides additional methods of use for these mini-promoter elements. For instance, it may be desirable to utilize the DCX mini-promoters of the present invention in a gene therapy or cell therapy application wherein the DCX mini-promoters are utilized to drive expression of a therapeutic or beneficial compound, such as a protein, in retinal ganglion or retinal amacrine cells. In such a way, the therapeutic or beneficial compound may be useful for a disease or condition that involves such retinal cells, or which may be improved by expression of the therapeutic or beneficial compound in those cells. In certain embodiments of the invention, there is thus provided a method of treatment of a subject having a disease or condition of the eye, the method comprising administering to the subject a therapeutically effective dose of a composition comprising a DCX mini-promoter element, wherein the DCX mini-promoter element comprises a DCX regulatory element operably linked in a non-native conformation to a DCX basal promoter element. In another embodiment, the DCX mini-promoter comprises a DCX basal promoter. The DCX mini-promoter element may have a nucleic acid sequence substantially similar in sequence and function to SEQ ID NO: 1-5. The DCX regulatory element may have a nucleic acid sequence substantially similar in sequence and function to SEQ ID NO: 6, 7, or 8. The DCX basal promoter element may have a nucleic acid sequence substantially similar in sequence and function to SEQ ID NO: 3, 4, or 5. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

The inventors herein further describe the present invention by way of the following non-limiting examples:

WORKING EXAMPLES

General Methods

Expression Vector

Figure 8:
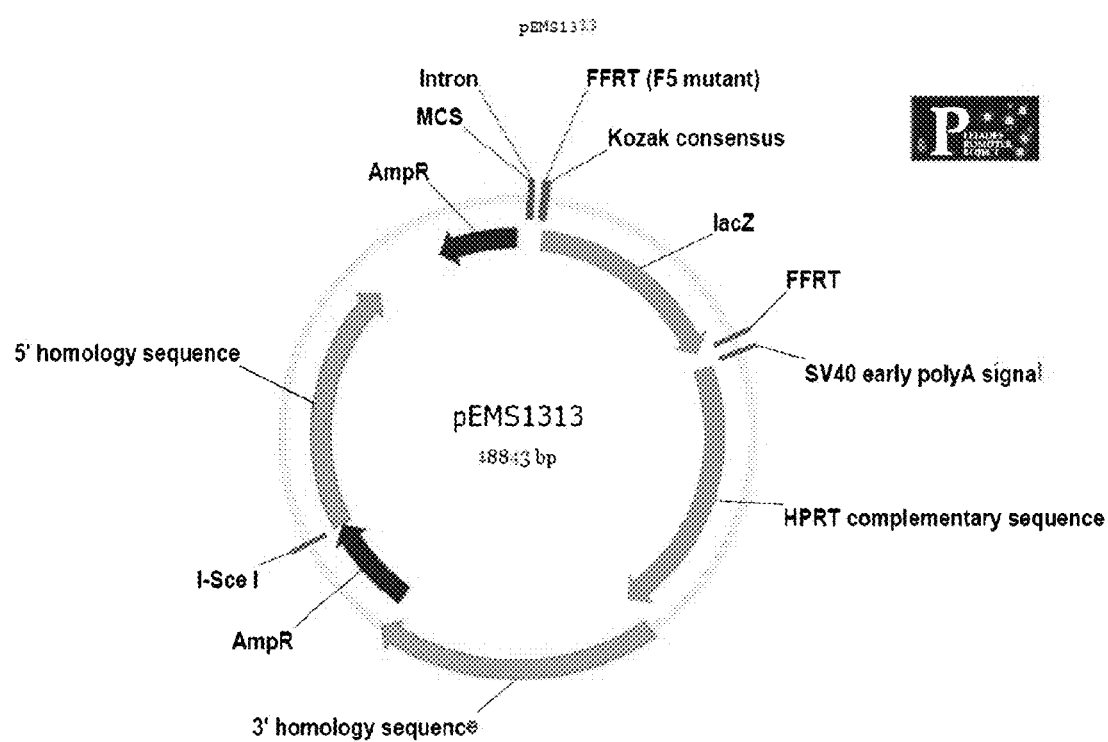
FIG. 8—DNA expression vector (pEMS1313) into which DCX promoter elements were inserted for expression studies. The DCX promoter with a nucleic acid sequence corresponding to SEQ ID NO: 1, 2, 3, 4 or 5 was inserted into the multiple cloning site (MCS) of the pEMS1313 vector such that it became operably linked to the lac Z reporter gene. The final construct, called Ple54 (containing SEQ ID NO: 1), Ple55 (containing SEQ ID NO: 2), Ple53 (containing SEQ ID NO: 3), Ple302 (containing SEQ ID NO: 4), Ple312 (SEQ ID NO: 5) also contained the HPRT genomic targeting sequence, an ampicillin resistance gene (AmpR) for screening, and a transcriptional termination sequence (SV40 polyA), as well as other elements necessary for vector replication and gene expression.

The nucleic acid fragment corresponding to SEQ ID NO: 1-5 was inserted into the multiple cloning site of pEMS1313 (driving the lacZ reporter, see FIG. 8) to produce the expression vectors (called Ple54, Ple55, Ple53, Ple302, and Ple316, respectively) used in the experiments.

Derivation of mEMS1202 Embryonic Stem Cells

Blastocysts were obtained from natural mating of B6-Hprtb-m3 homozygous females to 129-ROSA26 heterozygous males at 3.5 dpc. Blastocysts were flushed from uterine horns as per (Hogan, Beddington et al. 1994), cultured in EmbryoMax® KSOM with ½ Amino Acids, Glucose and Phenol Red (Cat # MR-121, Millipore/Chermicon, Temecula, Calif.) for 3-5 h, and then transferred onto mitomycin C (mitC; Cat#M4287, Sigma, Oakville, ON) mitotically inactivated B6-Hprtb-m3, B6129F1, or 129 mouse embryonic feeders (MEFs) derived from 13.5-day post-coital embryos (Ponchio, Duma et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng, Dutra et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well-developed ICM (inner cell mass) were treated with 20 µl 0.25% trypsin-EDTA (Invitrogen, Burlington, ON) for 5 min at 37° C., triturated with a 200 µl Pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON), 1000 U ESGRO-LIF (Millipore, ESG1107) and 0.01% β-mercaptoethanol (Sigma, Oakville, ON)) in 25%, 50%, 75% proportions (respectively) to adapt the cells to FBS-containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sortm1Sor and WT alleles and Hprtb-m3 and WT alleles. B6129F1-Gt(ROSA) 26Sortm1Sor/+, Hprtb-m3/Y (mEMS1204 series) and B6129F1-Gt(ROSA)26Sortm1Sor+/+, Hprtb-m3/Y (mEMS1202 series) cell lines were identified.

Knock-in at the Hprt Locus

The expression vector plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. Ple155 was targeted in our in-house derived mEMS1202 cell line. ESCs were grown to confluence on 4-6 T75 flasks of mitC treated Hprtb-m3 mouse embryonic feeders (MEFs) in FBS-ESC media. ESCs (1.7-2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml per 100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3rd day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of Knock-in Mice

Chimeric mice from targeted ESCs were generated by microinjection (Hogan, Beddington et al. 1994) into E3.5 blastocysts followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant Aw (white bellied agouti) allele, making the progeny appear brown with a cream belly, or in the latter case by the combination of Aw and Tyrc-ch (chinchilla), making the progeny appear golden. Non-germline progeny from the cross to B6 were homozygous for the recessive a (nonagouti) allele and appeared black, whereas non-germline progeny from the cross to B6-Alb were homozygous for the recessive Tyrc-2J (albino 2 Jackson) allele and appeared white.

Male chimeras derived from the cell lines were mated with B6-Alb females, and germline transmission identified by the presence of the dominant Tyr+ (tyrosinase; wild type) and the Aw (white bellied agouti) or a (nonagouti) alleles making the progeny appear brown with a cream belly or black, respectively. Non-germline progeny were homozygous for the recessive Tyrc-2J (albino 2 Jackson) allele and appeared white. All germline female offspring carry the knock-in X Chromosome and were mated with B6 males.

N2 offspring were analyzed for the presence of the KI allele by PCR.

Reporter Gene Detection

Adult male hemizygous MiniPromoter and age matched control mice were perfused with 4% paraformaldehyde (PFA) as previously described (Young, Berry et al. 2002). Whole brains and eyes were dissected out and post-perfusion immersion fixed with PFA for 2 hours at 4° C. The brains were sectioned using a coronal or sagittal brain mold (Electron Microscopy Sciences) at 1 mm and sections were placed in 12-well tissue culture plates. One whole eye and one half-cut eye, using a razorblade, was also placed in the plate. LacZ expression was detected by using 5-bromo-4-chloro-3-indolyl-β-D-galactopyranoside (X-Gal) as the substrate. The X-Gal staining solution contained the following: 1.0 mg/ml X-Gal, 2 mM potassium ferricyanide, 2 mM potassium ferrocyanide, and 40 mM MgCl2 in PBS. In brief, brain sections were rinsed with phosphate buffered saline (PBS), then incubated with X-Gal (Boeringer Mannheim, Indianapolis, Ind.) at 37° C., usually overnight. After staining the tissue was rinsed with PBS and moved into PBS containing 0.02% azide for storage. Eyes were further processed by post-fixing with 4% PFA for 2 hours at room temperature. After fixation, eyes were rinsed with PBS and cryoprotected in 25% sucrose-PBS at 4° C. overnight. Eyes were removed from the solution and blotted with a KimWipe before embedment in Optimal Cutting Temperature (OCT) alongside positive and negative controls. 12 µm sections were taken using a Microm HM 550 cryostat and directly mounted onto SuperFrost Plus microscope slides. Bright field images were taken on a Leica MZ125 dissecting microscope and photographed using an Olympus Coolsnap cf color camera with the ImagePro software package.

Example 1

Selection of DCX Mini-Promoter Elements

Two different DCX basal promoter regions were selected and tested, while three different regulatory regions of the human DCX promoter region were selected. The basal promoters included two shorter basal promoter (SEQ ID NO: 4, Ple302; SEQ ID NO: 5, Ple312), and a longer basal promoter (SEQ ID NO: 3, Ple53). Experiments also included one of the shorter basal promoters (SEQ ID NO: 4) fused to both regulatory region 1 (SEQ ID NO: 6) and regulatory region 2 (SEQ ID NO: 7), called Ple54; as well as the shorter basal promoter (SEQ ID NO: 4) fused to regulatory region 3 (SEQ ID NO: 8), called Ple55.

Example 2

Expression of Reporter in Brain by Ple53, Ple54, and Ple55

Figure 4:
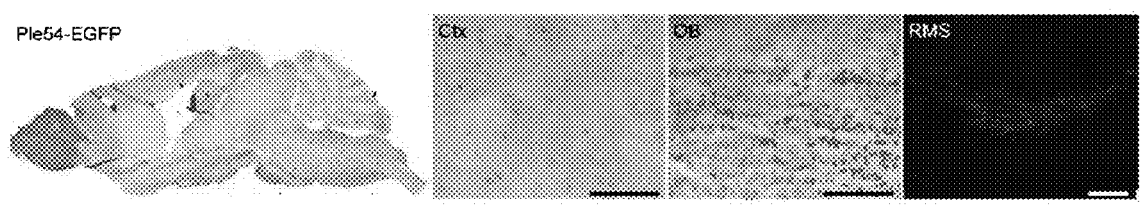
FIG. 4—Ple54-lacZ (DCX) expression in the brain. Mice were perfused and brains sectioned at 25 μm. EGFP is detected using anti-GFP immunochemistry (brown). Ple54-EGFP (DCX) expression is observed in different regions of the brain, including neurogenic areas, with enrichment in the OB as seen in the whole brain image. The last image shows co-staining of EGFP (green) with the endogenous Dcx protein (red) in the RMS. Ctx, cortex; OB, olfactory bulb; RMS, rostral migratory stream. Scale bars 100 μm.
Figure 5:
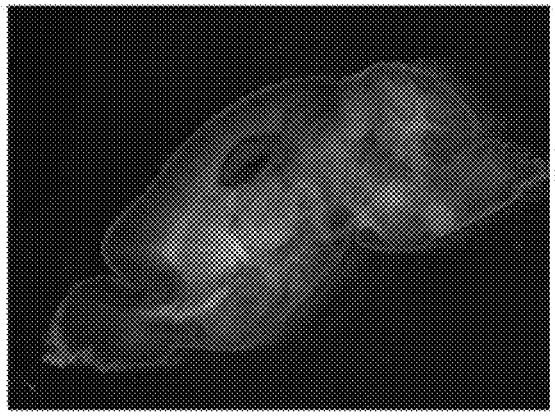
FIG. 5—Ple55-lacZ (DCX) expression in the brain. Mice were perfused, brains harvested and stained with X-gal. Expression of β-galactosidase from the MiniPromoter as detected by X-gal substrate is shown in blue. Neurogenic regions (SVZ, SGZ and RMS) are positive. All layers of the cortex are stained, the olfactory bulbs, and in most mid- and hind-brain regions, including parts of the cerebellum. The medial and lateral habenula is strongly positive. Expression is weak in the striatum and low in the central to posterior thalamic regions. White matter regions are labeled. SVZ, subventricular zone; SGZ, subgranular zone; RMS, rostral migratory stream.
Figure 5:
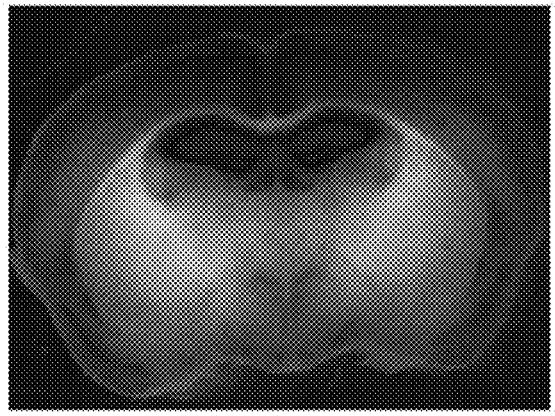
Figure 6:
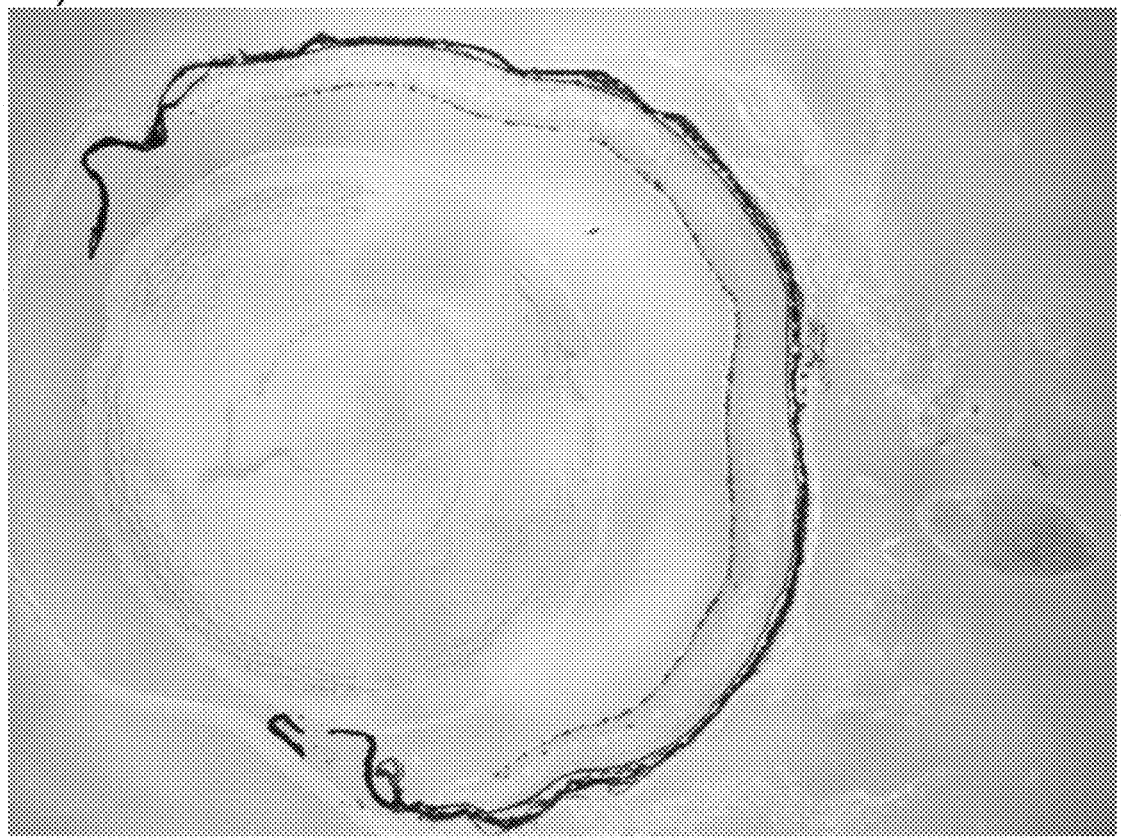
FIG. 6—Ple55-lacZ (DCX) expression in the eye. Eyes were perfused and stained with X-gal to detect β-galactosidase expression from the MiniPromoter. After staining, eyes were cryoprotected and sectioned at 12 µm and imaged. Expression is observed in the innermost aspect of the retina and in the optic nerve.
Figure 7:
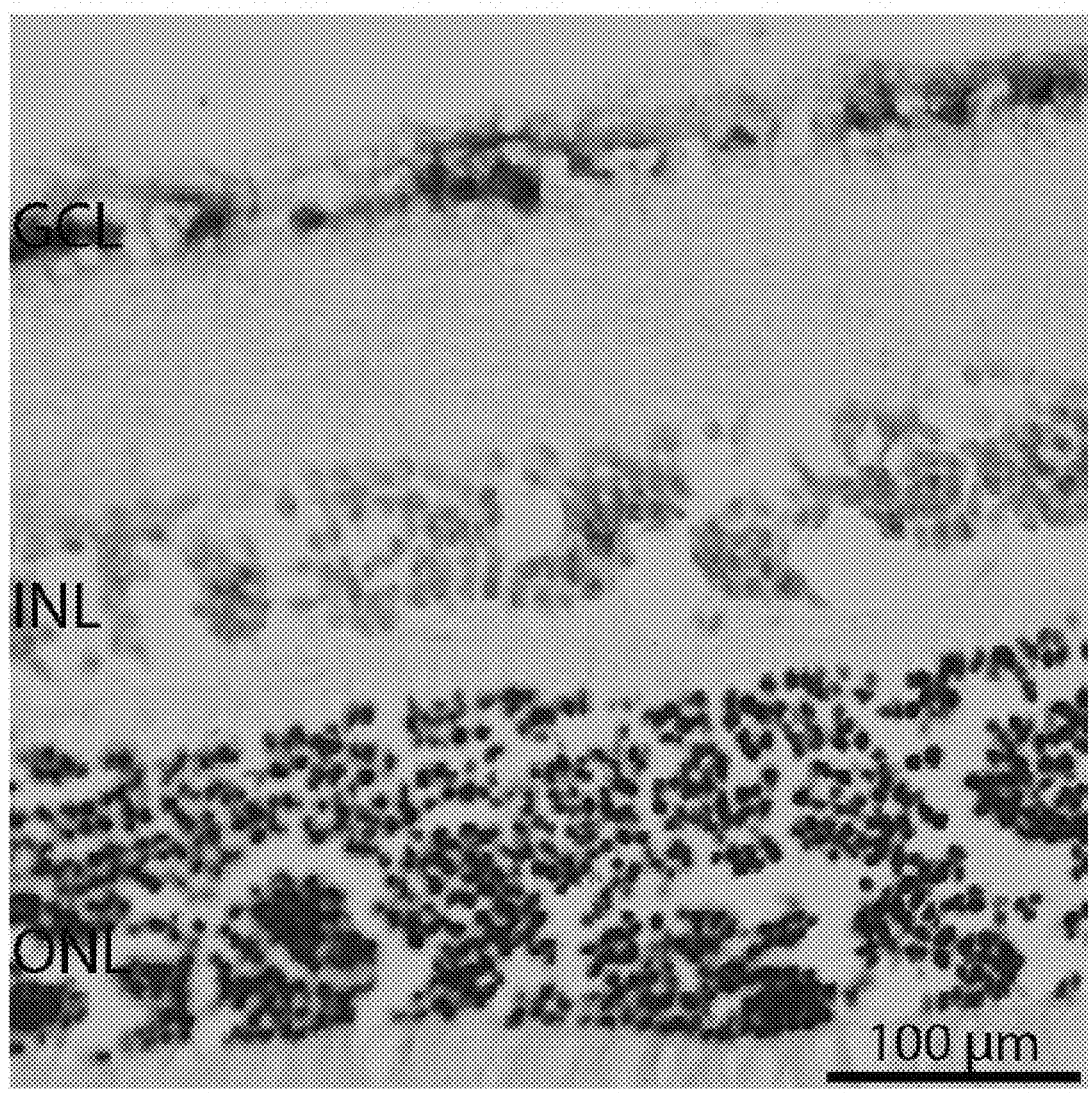
FIG. 7—Ple55-lacZ (DCX) expression is localized to the ganglion cell layer of the retina. Eyes were perfused and stained with X-gal to detect β-galactosidase expression from the MiniPromoter. After staining, eyes were cryoprotected and sectioned at 12 µm and counterstained with neutral red to indicate cell nuclei. The ganglion cell layer is where the predominant staining (blue) is observed. GCL, ganglion cell layer; INL, inner nuclear layer; ONL, outer nuclear layer. Scale bar 100 µm.

The Ple53, Ple54, and Ple55 expression vectors were introduced into mouse embryonic stem cells (ESCs) at the HPRT locus. The ESCs were used to generate genetically modified mice containing DCX. Immunohistochemical and immunofluorescence analysis of mouse brain tissue slices revealed lacZ reporter expression in the brain (see FIGS. 1, 4, and 5). All three constructs drove expression in DCX-positive neurogenic regions of the adult brain (rostral migratory stream, subventricular zone, and subgranular zones). Ple53 expression, as detected by X-gal and counter-stained with neutral red, was limited to the deepest cortical layer VI. Rare positive cells in layers II, IV and V are observed. However, Ple55 contained positive cells in all cortical layers, including layer I. Nearly all layer II, IV and VI neurons are labeled.

Example 3

Expression of Reporter in Eye by Ple53 and Ple55

The Ple53, Ple54, and Ple55 expression vectors were introduced into mouse embryonic stem cells (ESCs) at the HPRT locus. The ESCs were used to generate genetically modified mice containing DCX. Immunohistochemical and immunofluorescence analysis of mouse eye tissue slices revealed lacZ reporter expression in the eye (see FIGS. 1, 4, and 5). Both constructs expressed in the retinal ganglion cell layer (GCL; different from the hippocampal GCL), with rare putative amacrine cells observed in the inner nuclear layer (INL). The expression pattern was consistent with retinal ganglion cell (RGC) and/or amacrine cell identity. We then analyzed endogenous mouse DCX expression in the retina and did not find any positive signal in the adult, suggesting the expression patterns from Ple53 and Ple55 are unique and unexpected.

What is claimed is:

1. An isolated polynucleotide comprising a DCX mini-promoter wherein the DCX mini-promoter comprises a DCX regulatory element with substantial similarity to SEQ ID NO: 6, 7 or 8 operably joined to an DCX basal promoter with substantial similarity to SEQ ID NO: 4 or 5 wherein the spacing between the DCX regulatory element and the DCX basal promoter is not more than 500 nucleotides (nt).

2. The polynucleotide of claim 1 comprising a DCX mini-promoter with substantially similarity to SEQ ID NO: 1.

3. The polynucleotide of claim 1 comprising a DCX mini-promoter with substantial similarity to SEQ ID NO: 2.

4. The isolated polynucleotide of claim 1, operably linked to an expressible sequence.

5. A vector comprising the isolated polynucleotide of claim 1.

6. An isolated cell comprising the vector of claim 5.

7. The cell of claim 6, wherein the vector is stably integrated into the genome of the cell.

8. The cell of claim 6 or claim 7, wherein the cell is a stem cell or a retinal cell.

9. A method of expressing a sequence of interest, the method comprising operably linking the sequence of interest to the polynucleotide of claim 1; and introducing into a cell permissive for expression from the DCX mini-promoter.

10. An isolated polynucleotide comprising a DCX mini-promoter wherein the DCX mini-promoter comprises a DCX regulatory element with at least 95% sequence identity to SEQ ID NO: 6, 7 or 8 operably joined to an DCX basal promoter with at least 95% sequence identity to SEQ ID NO: 4 or 5, wherein the spacing between the DCX regulatory element and the DCX basal promoter is not more than 500 nucleotides (nt).

11. The polynucleotide of claim 10, wherein the DCX mini-promoter has at least 95% sequence identity to SEQ ID NO: 1.

12. The polynucleotide of claim 10 wherein the DCX mini-promoter has at least 95% sequence identity to SEQ ID NO: 2.

13. The isolated polynucleotide of claim 10, operably linked to an expressible sequence.

14. A vector comprising the isolated polynucleotide of claim 10.

15. An isolated cell comprising the vector of claim 14.

16. The cell of claim 15, wherein the vector is stably integrated into the genome of the cell.

17. The cell of claim 15, wherein the cell is a stem cell or a retinal cell.

18. A method of expressing a sequence of interest, the method comprising operably linking the sequence of interest to the polynucleotide of claim 10; and introducing into a cell permissive for expression from the DCX mini-promoter.

* * * * *